(12) United States Patent
Duffy et al.

(10) Patent No.: US 9,795,482 B2
(45) Date of Patent: Oct. 24, 2017

(54) PROSTHETIC HEART VALVE DEVICES AND METHODS OF VALVE REPAIR

(75) Inventors: Niall Duffy, County Galway (IE); Yueqiang Xue, County Galway (IE); Luke Hughes, County Galway (IE)

(73) Assignee: Medtronic, Inc., Minneapolis, MN (US)

(*) Notice: Subject to any disclaimer, the term of this patent is extended or adjusted under 35 U.S.C. 154(b) by 1141 days.

(21) Appl. No.: 12/768,124

(22) Filed: Apr. 27, 2010

(65) Prior Publication Data

US 2011/0264208 A1    Oct. 27, 2011

(51) Int. Cl.
*A61F 2/24*    (2006.01)
*A61B 17/08*    (2006.01)

(52) U.S. Cl.
CPC .......... *A61F 2/2457* (2013.01); *A61F 2/2454* (2013.01); *A61B 2017/088* (2013.01); *A61F 2220/0016* (2013.01); *A61F 2220/0025* (2013.01); *A61F 2250/0007* (2013.01)

(58) Field of Classification Search
CPC ............ A61B 2017/088; A61F 2/2454; A61F 2/2457; A61F 2220/0016; A61F 2220/0025; A61F 2220/0033; A61F 2250/0007
USPC ................ 623/2.1, 2.37–2.39, 2.42
See application file for complete search history.

(56) References Cited

U.S. PATENT DOCUMENTS

| | | | |
|---|---|---|---|
| 3,874,388 A * | 4/1975 | King et al. | 606/232 |
| 5,342,393 A * | 8/1994 | Stack | 606/213 |
| 5,944,738 A * | 8/1999 | Amplatz et al. | 606/213 |
| 6,210,432 B1 | 4/2001 | Solem et al. | |
| 6,332,893 B1 | 12/2001 | Mortier et al. | |
| 6,602,288 B1 | 8/2003 | Cosgrove et al. | |
| 6,629,534 B1 * | 10/2003 | St. Goar et al. | 128/898 |
| 6,702,835 B2 | 3/2004 | Ginn | |
| 6,723,038 B1 | 4/2004 | Schroeder et al. | |
| 6,776,784 B2 | 8/2004 | Ginn | |
| 6,962,605 B2 | 11/2005 | Cosgrove et al. | |
| 6,986,775 B2 | 1/2006 | Morales et al. | |
| 6,989,028 B2 | 1/2006 | Lashinski et al. | |
| 6,997,950 B2 | 2/2006 | Chawla | |
| 6,997,951 B2 | 2/2006 | Solem et al. | |
| 7,011,682 B2 | 3/2006 | Lashinski et al. | |
| 7,037,334 B1 | 5/2006 | Hlavka et al. | |
| 7,044,967 B1 | 5/2006 | Solem et al. | |
| 7,056,325 B1 | 6/2006 | Makower et al. | |
| 7,090,695 B2 | 8/2006 | Solem et al. | |
| 7,166,127 B2 | 1/2007 | Spence et al. | |
| 7,211,110 B2 | 5/2007 | Rowe et al | |
| 7,220,265 B2 | 5/2007 | Chanduszko et al. | |

(Continued)

FOREIGN PATENT DOCUMENTS

WO    2008/129405    10/2008

*Primary Examiner* — Paul Prebilic (57) ABSTRACT

A mechanism for adjusting the chordae connecting the leaflets of a mitral valve to the papillary muscles in order to restore normal functioning of the mitral valve. The devices or mechanisms can correct problems associated with both prolapsed leaflets and restricted leaflets to allow the leaflets to properly coapt, thereby preventing or minimizing regurgitation. In accordance with the invention, the mechanisms or devices used for adjusting the chordae can be delivered and implanted in a minimally invasive and/or percutaneous manner, such as via transapical methods, transfermoral methods, or trans-septal methods.

10 Claims, 8 Drawing Sheets

(56) References Cited

U.S. PATENT DOCUMENTS

| | | |
|---|---|---|
| 7,296,577 B2 | 11/2007 | Lashinski et al. |
| 7,311,728 B2 | 12/2007 | Solem et al. |
| 7,431,692 B2 | 10/2008 | Zollinger et al. |
| 7,431,726 B2 | 10/2008 | Spence et al. |
| 7,588,582 B2 | 9/2009 | Starksen et al. |
| 7,635,386 B1 | 12/2009 | Gammie |
| 7,637,945 B2 | 12/2009 | Solem et al. |
| 7,666,193 B2 | 2/2010 | Starksen et al. |
| 7,699,892 B2 | 4/2010 | Rafiee et al. |
| 7,717,954 B2 | 5/2010 | Solem et al. |
| 7,758,637 B2 | 7/2010 | Starksen et al. |
| 8,021,421 B2* | 9/2011 | Fogarty et al. .............. 623/2.38 |
| 8,083,793 B2* | 12/2011 | Lane et al. ................... 623/2.38 |
| 2002/0058994 A1* | 5/2002 | Hill et al. ..................... 623/2.11 |
| 2003/0105519 A1 | 6/2003 | Fasol et al. |
| 2004/0088047 A1* | 5/2004 | Spence et al. ............... 623/2.36 |
| 2004/0133236 A1* | 7/2004 | Chanduszko ................. 606/213 |
| 2004/0193191 A1 | 9/2004 | Starksen et al. |
| 2004/0220596 A1 | 11/2004 | Frazier et al. |
| 2004/0243227 A1 | 12/2004 | Starksen et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0177180 A1 | 8/2005 | Kaganov et al. |
| 2005/0187568 A1 | 8/2005 | Klenk et al. |
| 2005/0197696 A1 | 9/2005 | Duran |
| 2005/0267495 A1 | 12/2005 | Ginn et al. |
| 2005/0273138 A1 | 12/2005 | To et al. |
| 2006/0025787 A1 | 2/2006 | Morales et al. |
| 2006/0052821 A1 | 3/2006 | Abbott et al. |
| 2006/0095025 A1 | 5/2006 | Levine et al. |
| 2006/0129235 A1* | 6/2006 | Seguin et al. ................ 623/2.11 |
| 2006/0282161 A1* | 12/2006 | Huynh et al. ................ 623/2.11 |
| 2007/0010857 A1 | 1/2007 | Sugimoto et al. |
| 2007/0055206 A1 | 3/2007 | To et al. |
| 2007/0073315 A1 | 3/2007 | Ginn et al. |
| 2007/0112424 A1 | 5/2007 | Spence et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0255315 A1* | 11/2007 | Buckman et al. ............ 606/218 |
| 2007/0265658 A1* | 11/2007 | Nelson et al. ................ 606/213 |
| 2008/0195126 A1* | 8/2008 | Solem .......................... 606/155 |
| 2008/0228032 A1 | 9/2008 | Starksen et al. |
| 2008/0228165 A1 | 9/2008 | Spence et al. |
| 2008/0228265 A1 | 9/2008 | Spence et al. |
| 2008/0228266 A1 | 9/2008 | McNamara et al. |
| 2008/0228267 A1 | 9/2008 | Spence et al. |
| 2008/0234701 A1 | 9/2008 | Morales et al. |
| 2008/0234702 A1 | 9/2008 | Morales et al. |
| 2008/0234704 A1 | 9/2008 | Starksen et al. |
| 2008/0234728 A1 | 9/2008 | Starksen et al. |
| 2008/0234815 A1 | 9/2008 | Starksen |
| 2008/0243150 A1 | 10/2008 | Starksen et al. |
| 2008/0275503 A1 | 11/2008 | Spence et al. |
| 2008/0294177 A1 | 11/2008 | To et al. |
| 2009/0076547 A1 | 3/2009 | Sugimoto et al. |
| 2009/0209950 A1 | 8/2009 | Starksen |
| 2009/0222083 A1 | 9/2009 | Nguyen et al. |
| 2009/0234318 A1 | 9/2009 | Loulmet et al. |
| 2010/0023056 A1 | 1/2010 | Johansson et al. |
| 2010/0030328 A1 | 2/2010 | Seguin et al. |
| 2010/0070028 A1 | 3/2010 | Sugimoto |
| 2010/0094248 A1 | 4/2010 | Nguyen et al. |
| 2010/0161042 A1 | 6/2010 | Maisano et al. |
| 2010/0298929 A1* | 11/2010 | Thornton et al. ............. 623/2.1 |

* cited by examiner

PROSTHETIC HEART VALVE DEVICES AND METHODS OF VALVE REPAIR

TECHNICAL FIELD

The present invention relates generally to devices and methods for repair of heart valves, and more particularly to devices and methods for use in repair of the mitral valve.

BACKGROUND

One of the two atrio-ventricular valves in the heart is the mitral valve, which is located on the left side of the heart and which forms or defines a valve annulus and valve leaflets. The mitral valve is located between the left atrium and the left ventricle, and serves to direct oxygenated blood from the lungs through the left side of the heart and into the aorta for distribution to the body. As with other valves of the heart, the mitral valve is a passive structure in that it does not itself expend any energy and does not perform any active contractile function.

The mitral valve includes two moveable leaflets that open and close in response to differential pressures on either side of the valve. Ideally, the leaflets move apart from each other when the valve is in an open position, and meet or "coapt" when the valve is in a closed position. However, problems can develop with valves, which can generally be classified as either stenosis, in which a valve does not open properly, or insufficiency (also called regurgitation), in which a valve does not close properly. Stenosis and insufficiency may occur concomitantly in the same valve. The effects of valvular dysfunction vary, with mitral regurgitation or backflow typically having relatively severe physiological consequences to the patient. Regurgitation, along with other abnormalities of the mitral valve, can increase the workload placed on the heart. The severity of this increased stress on the heart and the patient, and the ability of the heart to adapt to it, determine the treatment options that are available for a particular patient. In some cases, medication can be sufficient to treat the patient, which is the preferred option when it is viable; however, in many cases, defective valves have to be repaired or completely replaced in order for the patient to live a normal life.

One situation where repair of a mitral valve is often viable is when the defects present in the valve are associated with dilation of the valve annulus, which not only prevents competence of the valve but also results in distortion of the normal shape of the valve orifice. Remodeling of the annulus is central to these types of reconstructive procedures on the mitral valve. When a mitral valve is repaired, the result is generally a reduction in the size of the posterior segment of the mitral valve annulus. As a part of the mitral valve repair, the involved segment of the annulus is diminished (i.e., constricted) so that the leaflets may coapt correctly on closing, and/or the annulus is stabilized to prevent post-operative dilatation from occurring. Either result is frequently achieved by the implantation of a prosthetic ring or band in the supra annular position, which can restrict, remodel and/or support the annulus to correct and/or prevent valvular insufficiency.

As an alternative to remodeling of the mitral valve annulus in some cases, the chordae tendinae (referred to herein as "chordae") that are attached to the leaflets of the mitral valve can be repaired by surgical replacement of the native chordae with artificial chordae in an attempt to restore normal function to the leaflets. With these types of procedures, at least a portion of one or both of the mitral leaflets are secured to one or more structures within the heart using artificial chord members that have a length that allows the leaflets to open and close normally. These procedures can involve the implantation of sutures, which may be made of ePTFE, for example, and which are attached within the heart using relatively labor-intensive and technically challenging procedures. Such procedures are typically performed using invasive, open-heart surgical procedures that require opening of the thoracic cavity to gain access to the heart, then stopping the heart while utilizing heart bypass procedures. However, the use of such bypass techniques can be traumatic and risky for the patient, particularly in cases where the surgical heart repair process takes a long period of time.

To simplify surgical procedures and reduce patient trauma, there has been a recent increased interest in minimally invasive and percutaneous replacement and/or repair of cardiac valves. Replacement or repair of a heart valve in this way typically does not involve actual physical removal of the diseased or injured heart valve. Instead, in one example, a replacement valve can be delivered in a compressed condition to a valve site, such as the pulmonary or aortic valve site, where it is expanded to its operational state. However, percutaneous replacement of a valve and/or minimally invasive valve repair in the area of the mitral valve has its own unique considerations due to the different physical characteristics of the mitral valve as compared to the pulmonary and aortic valves. There is a continued desire to be able to be able to improve mitral valve repair and replacement devices and procedures to accommodate the physical structure of the heart without causing undue stress during surgery, such as providing devices and methods for repairing the mitral valve in a minimally invasive and/or percutaneous manner.

SUMMARY

One embodiment of the invention includes a mechanism for adjusting the chordae that connect the leaflets of a mitral valve to the papillary muscles in order to restore normal functioning of the mitral valve. These devices or mechanisms can correct problems associated with both prolapsed leaflets and restricted leaflets to allow the leaflets to properly coapt, thereby preventing or minimizing regurgitation. In accordance with the invention, the mechanisms or devices used for adjusting the chordae can be delivered and implanted in a minimally invasive and/or percutaneous manner, such as via transapical methods, transfermoral methods, or trans-septal methods.

In one embodiment of the invention, a device is provided that comprises a wire with a first anchor that engages with a leaflet of a mitral valve, and a second anchor spaced from the first anchor that engages with the papillary muscle. In another embodiment, the device includes a wire with a first anchor that engages with a leaflet of a mitral valve and a second anchor spaced from the first anchor that engages with the wall of the heart at the apex. In yet another alternative embodiment, the device includes a wire that is anchored to the chordae that extend between the leaflets of the mitral valve and the papillary muscles. With any of these devices, once they are anchored relative to the heart in their desired position, they can be adjusted to provide the desired correction to the positioning of the mitral valve leaflets relative to each other and other structures of the heart.

Further in accordance with the invention, a number of different embodiments of anchoring mechanisms for chordae support devices are provided. For one example, a self-expanding "umbrella" is provided, which can anchor a wire to the mitral leaflet. For another example, a rivet type of mechanism is provided to anchor a wire to the valve leaflet wall. In particular, the rivet type mechanism can include a pull cord that provides adjustability to the device or can instead include a collapsible rivet portion. In yet another example, the anchoring mechanism can be a stapler type of device that is made of a material having shape memory characteristics. This mechanism can be pre-shaped into a loop, for example, and can have a sharp end that is used to penetrate a valve wall, and also includes a flat portion that provides a load distribution over the surface of the leaflet to prevent it from pulling back through the tissue. The loop shape can be straightened and held in this straightened condition during the delivery process, after which it can be allowed to return to its curved or looped shape in order to anchor it to the tissue of the valve wall.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
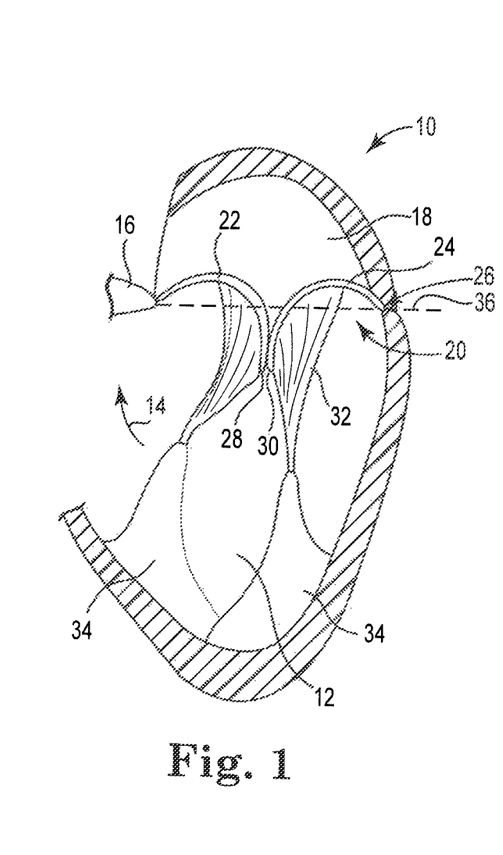
FIG. 1 is a schematic cross-sectional view of a portion of a heart, illustrating a properly functioning mitral valve during systole.

Referring now to the Figures, and initially to FIG. 1, a portion of a heart 10 is illustrated in systole. In particular, the portion of the heart 10 shown includes the left ventricle 12, which is contracting in this state of the heart to make blood flow in a direction indicated by arrow 14 toward the aortic valve 16. The heart 10 further includes a mitral valve 20 positioned between a left atrium 18 and the left ventricle 12. The mitral valve 20 includes a first leaflet 22 and a second leaflet 24, each of which extends at a first end from a mitral valve annulus 26 and terminates at a distal end 28, 30, respectively. When the mitral valve 20 is functioning properly, as in this figure, the distal ends 28, 30 of the leaflets 22, 24 and/or the areas of the leaflets immediately adjacent to the ends 28, 30 will meet or coapt to create a sealing region. A reference line 36 indicates the position of these leaflets 22, 24 relative to the annulus 26 when the mitral valve 20 is functioning properly. Back flow of blood or "regurgitation" through the mitral valve 20 is prevented during this systole phase due to the leaflets 22, 24 functioning as a check valve that prevents blood flow past the leaflets when the pressure in the left ventricle 12 is higher than the pressure in the left atrium 18. The mitral valve 20 further includes a number of chordae 32, each of which can include multiple branching tendons that are secured at one end over the lower surfaces of each of the leaflets 22, 24. The chordae 32 are attached at their opposite ends to the papillary muscles 34, which extend upwardly from the lower wall of the left ventricle 12.

Figure 2:
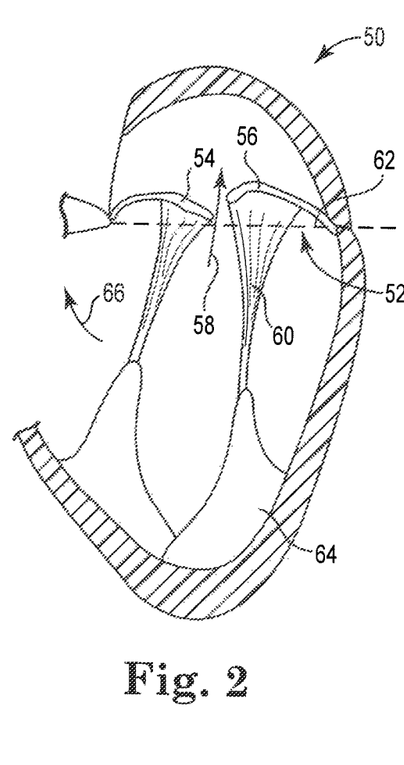
FIG. 2 is a schematic cross-sectional view of a portion of a heart, illustrating the mitral valve with prolapsed leaflets during systole.

FIG. 2 illustrates a heart 50 in systole, which is generally configured similar to the heart 10 of FIG. 1; however, heart 50 includes structural defects that allow for regurgitation or back flow of blood through a mitral valve 52. As shown, mitral valve 52 includes a first leaflet 54 and a second leaflet 56 that are attached to the papillary muscles 64 via chordae 60. At least some of the chordae 60 are damaged or otherwise compromised in such a way that they no longer provide adequate tension to the leaflets 54, 56, thereby allowing the leaflets to prolapse. A reference line 62 indicates the position of these leaflets 54, 56 relative to the mitral valve annulus when the mitral valve 52 is functioning properly, wherein the leaflets 54, 56 of this embodiment are prolapsed into the left atrium relative to the reference line 62. That is, when the heart is in systole, the leaflets 54, 56 do not properly meet or coapt, thereby allowing leakage of blood from the left ventricle into the left atrium during systole, in a direction illustrated by an arrow 58. Although a quantity of blood can still flow in a direction indicated by arrow 66 toward the aortic valve when the leaflets are prolapsed, even slight leakage of blood through the mitral valve 52 can be detrimental to proper functioning of the heart.

Figure 3:
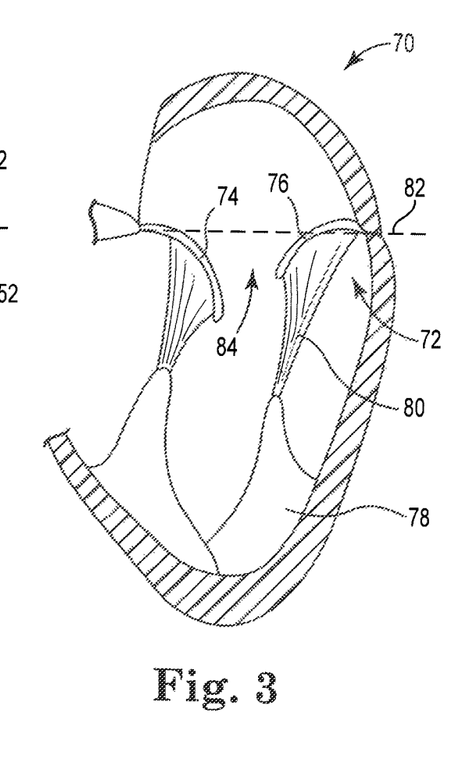
FIG. 3 is a schematic cross-sectional view of a portion of a heart, illustrating the mitral valve with restricted leaflets during systole.

FIG. 3 illustrates yet another heart 70 in systole, which is generally configured similar to the heart 10 of FIG. 1; however, heart 70 includes different structural defects that allow for regurgitation or back flow of blood through a mitral valve 72. As shown, mitral valve 72 includes a first leaflet 74 and a second leaflet 76 that are attached to the papillary muscles 78 via chordae 80. In this embodiment, the functioning of chordae 80 and/or the papillary muscles 78 is impaired (e.g., due to ischemic heart disease) such that they restrict the movement of the leaflets 74, 76 and prevent them from properly meeting or coapting with each other. Again, a reference line 82 indicates the position of the leaflets 74, 76 relative to the mitral valve annulus when the mitral valve 72 is functioning properly, wherein the leaflets 74, 76 of this embodiment are restricted from upward movement toward the annulus (and the reference line 82) by the papillary muscles 78 and/or chordae 80. The insufficient coaptation of the leaflets 74, 76 allows undesirable leakage of blood from the left ventricle to the left atrium (i.e., regurgitation), in a direction illustrated by arrow 84. It is noted that regurgitation can also be caused by other heart conditions, such as a condition known as cardiomyopathy, where the heart is dilated in such a way that its mitral valve annulus is enlarged, making it impossible for the leaflets to coapt during systole.

The devices and methods of the invention are provided for performing valve repairs in a minimally invasive and/or percutaneous manner, if desired. Advantageously, these devices and methods therefore can be used to avoid some of the drawbacks associated with more invasive open-heart surgical techniques. In addition, the devices and methods of the invention can provide more favorable surgical results since repairs can be performed while the heart is still beating, thereby providing the surgeon with immediate feedback during surgery on the results of the valve repair. The surgeon will then be able to adjust the devices until the desired result is achieved, rather than determining after the surgery is complete that further adjustments are needed.

The valve repair techniques of the invention involve accessing one or more areas of the heart by making at least one small incision, then inserting a delivery device and/or imaging equipment (e.g., an endoscope) to contact the heart. The desired repair area can then be accessed and the valve repair procedure can be performed. These methods can be performed in a completely percutaneous manner, such as via the femoral veins, via the inter-atrial septum (i.e., transseptal access) and into the left atrium, or via a retrograde approach, in which the femoral artery is accessed, across the aortic valve. In many cases, the devices and methods of the invention involve creating an access point in the apex region of the heart through which the defective valve (e.g., a regurgitating mitral valve) may be accessed, and then introducing a device through this access point in order to repair the valve. In some cases, it may be desirable to cut the native chordae either before or after completing the repair procedure, particularly in cases where the native chordae is causing restriction of the native mitral valve leaflet(s).

Figure 4:
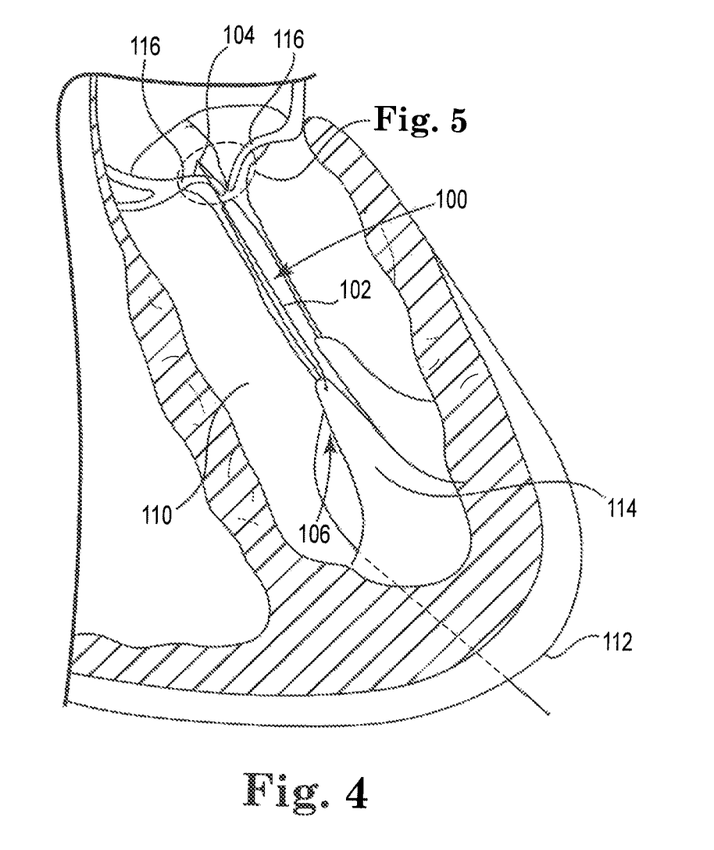
FIG. 4 is a schematic view of a portion of a heart and including one embodiment of a chordae support device between a papillary muscle and a leaflet of the mitral valve.
Figure 5:
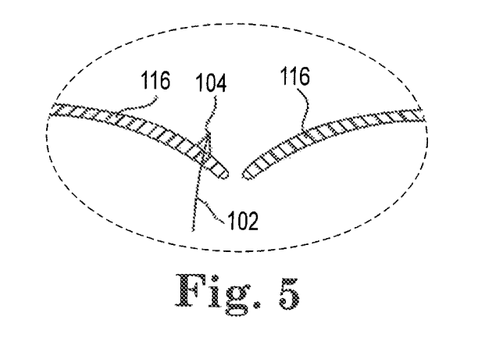
FIG. 5 is an enlarged schematic view of the mitral valve area indicated generally by a circle in FIG. 4 and including an anchor of the chordae support device.
Figure 6:
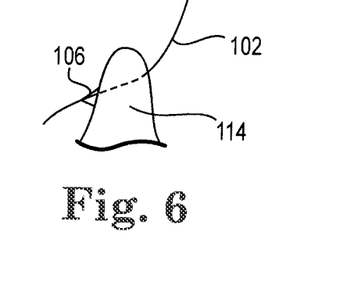
FIG. 6 is an enlarged schematic view of the papillary muscle area of FIG. 4 and including another anchor of the chordae support device.

FIGS. 4-6 illustrate one embodiment of an anchoring device 100 that is used to correct the length of the chordae that extends from a mitral valve leaflet to papillary muscles. In particular, the device 100 includes an elongated wire portion 102 and first and second anchor members 104, 106, respectively, which are spaced from each other along the wire portion 102. First anchor portion 104 includes a piercing member that tapers outwardly from a point such that when the point of the piercing member penetrates tissue and moves through it in a first direction, it cannot be pulled back in a direction that is opposite the first direction and through that same hole it entered. Second anchor portion 106 can be translated along the length of the wire portion 102 to provide the desired adjustability to the device 100, as described below relative to one exemplary method.

In such an exemplary repair method, device 100 can be implanted by accessing the left ventricle area 110 through an opening created in an apex 112 of the heart. The device 100 is moved through the opening in the apex 112 and directed through the ventricle 110 until it pierces the papillary muscle 114 at an access point and exits through an exit point. The device 100 will continue to be manipulated through the left ventricle 110 generally along the length of the native chordae, until it reaches one of the leaflets 116 of an improperly functioning mitral valve. The first anchor portion 104 can then pierce through the leaflet 116 from its bottom side (i.e., the ventricle side) to its top side (i.e., the atrial side) until a trailing side of the anchor portion 104 is adjacent to the top side of the leaflet 116. The second anchor portion 106 can then be slid upwardly toward the access point where the first anchor portion 104 penetrated the papillary muscle 114 until the second anchor portion 106 contacts the outer papillary muscle surface. Additional force can be placed on the anchor portion 106 to slide it even further toward anchor portion 104 and the leaflet 116 until the desired length of the wire portion 102 is achieved. That is, the device 100 acts to replace the native chordae by adjusting the length of wire portion 102 that is located between the first and second anchor portions 104, 106.

Once the anchor portion 106 is in its desired position relative to the length of the wire portion 102, it can be maintained in this position in a number of ways. For one example, the wire portion 102 can be provided with a ratcheting type of mechanism that allows the anchor portion 106 to only be slid in one direction along its length. In another example, there may be sufficient frictional force between the wire portion 102 and anchor portion 106 that the anchor portion 106 will remain generally fixed relative to the wire portion 102 without the application of a certain amount of additional force. In yet another example, the side of the anchor 106 that is pressed against the papillary muscle 114 will engage sufficiently with the muscle 114 that it cannot easily slide in the opposite direction along the wire portion 102.

Figure 7:
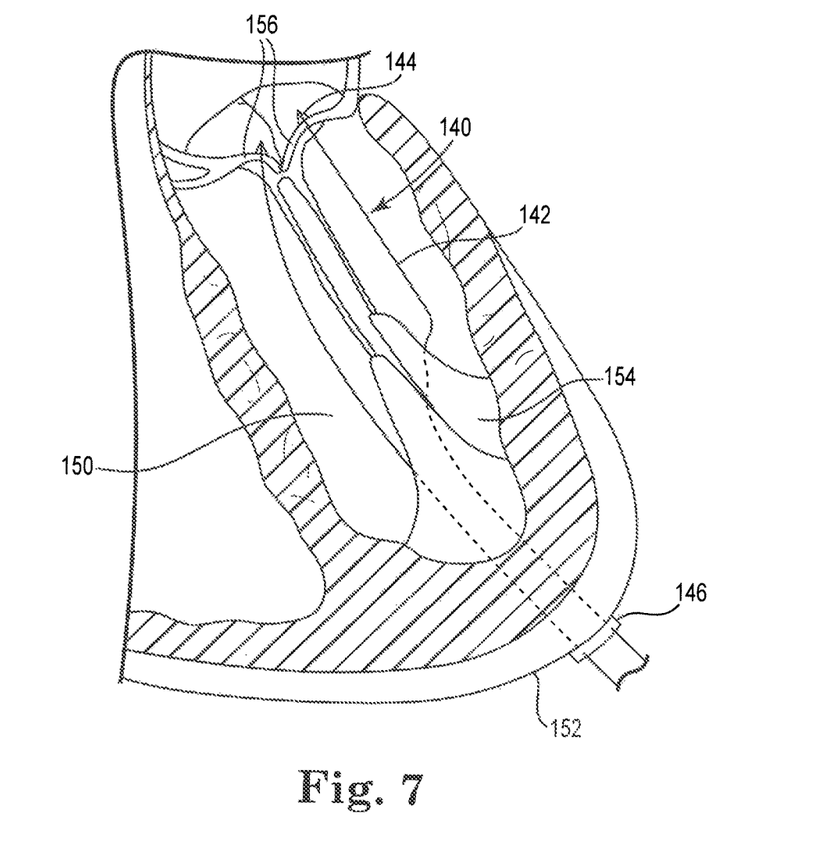
FIG. 7 is a schematic view of a portion of a heart and including another embodiment of a chordae support device between the papillary muscles and leaflets of a mitral valve.

FIG. 7 illustrates another exemplary embodiment of an anchoring device 140 that is used to correct the length of the chordae that extends from a mitral valve leaflet to papillary muscles. In particular, the device 140 includes an elongated wire portion 142 and first and second anchor members 144, 146, respectively, which are spaced from each other along the wire portion 142. First anchor portion 144 includes a piercing member that tapers outwardly from a point such that when the point of the piercing member penetrates tissue and moves through it in a first direction, it cannot be pulled back in a direction that is opposite the first direction and through that same hole it entered. Second anchor portion 146 can be translated along the length of the wire portion 142 to provide the desired adjustability to the device 140, as described below relative to one exemplary method.

In one exemplary repair method, device 140 can be implanted by accessing the left ventricle area 150 through an opening created in an apex 152 of the heart, as is described above relative to FIGS. 4-6. The device 140 is moved through the opening in the apex 152 and through the ventricle 150 until it pierces a papillary muscle 154. The device 140 will continue to be manipulated through the left ventricle 150 until it reaches one of the leaflets 156 of an improperly functioning mitral valve. The first anchor portion 144 can then pierce through one of the leaflets 156 until it is positioned on the side of leaflet 156 that faces toward the left atrium. The second anchor portion 146, which is positioned on the outside of the apex 152, can then be slid upwardly toward the access point into the apex 152 until it contacts the outer apex wall. Additional force can be put on the anchor portion 146 to slide it even further toward anchor portion 144 and the leaflet 156 until the desired length of the wire portion 142 between first and second anchor members 144, 146 is achieved. Once the anchor portion 146 is in its desired position relative to the length of the wire portion 142, it can be maintained in this position in a number of ways, such as those described above relative to the second anchor portion 106, for example.

Figure 8:
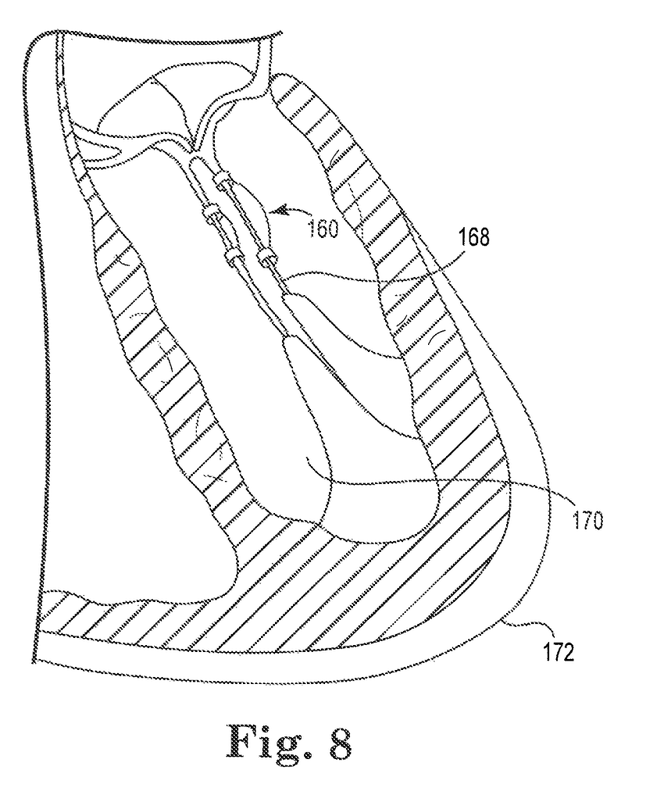
FIG. 8 is a schematic view of a portion of a heart and including yet another embodiment of a chordae support device.
Figure 9:
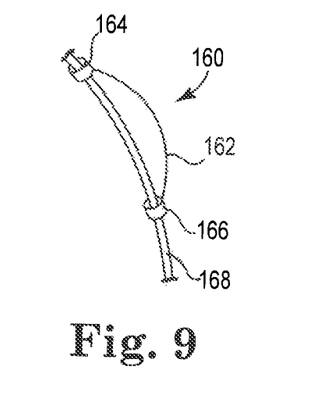
FIG. 9 is an enlarged schematic view of the chordae support device of FIG. 8 as it can be positioned relative to the chordae.

FIG. 7 illustrates two devices for providing chordae support within a single heart, with one device being provided for each of the leaflets, although it is possible that only one of the leaflets will be repaired using the devices of the invention. It is further illustrated that a single anchor portion 146 is being used at the adjustment end for both of the two chordae adjustment devices, although it is understood that each of these devices can instead have its own anchor portion in the area of the apex. It is understood that one or more of these devices can be used for either or both of the leaflets, and/or that more than one type of chordae support device may be used within a single heart, such as different types of devices that are described herein FIGS. 8 and 9 illustrate another exemplary embodiment of an anchoring device 160 that is used to modify the length of certain chordae 168 that extend from a mitral valve leaflet to papillary muscles. In particular, the device 160 includes a wire segment 162 and first and second anchor members 164, 166, respectively, which are spaced from each other along the wire portion 162. Anchor members 164, 166 each comprise a spring-loaded anchor that can lock onto the native chordae 168. Once the device 160 is attached to the chordae, it is possible to slide the anchor members 164, 166 along the chordae to which they are attached in order to adjust the distance between them, thereby changing the overall length of the native chordae 168 to which they are attached.

One or more of the devices 160 can be delivered to their desired location via a delivery system with the devices being under tension, such that when a delivery sheath is pulled away from a device 160 to expose it, the anchor members 164, 166 can spring shut and their barbs can anchor onto the chordae. In such an exemplary repair method, device 160 can be implanted by accessing the left ventricle area 170 through an opening created in an apex 172 of the heart, for example. The device 160 can be moved through the opening in the apex 172 and through the ventricle 170 until it reaches the chordae to which it will be attached. At that point, the device 160 can be deployed in the manner described above.

Figure 10:
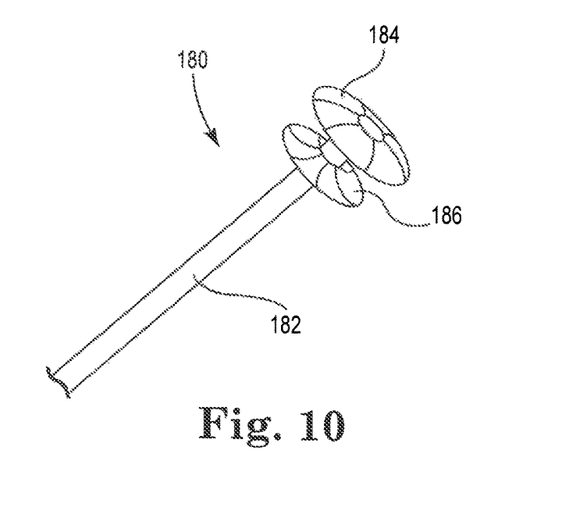
FIG. 10 is a perspective view of an embodiment of an anchoring device for securing a chordae support device to tissue.
Figure 11:
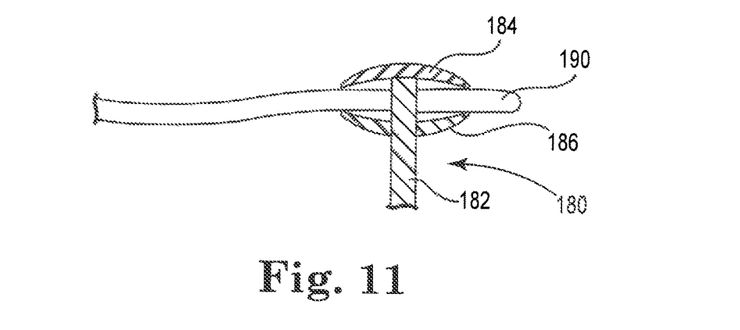
FIG. 11 is a cross-sectional schematic view of the anchoring device of FIG. 10 attached to a piece of tissue.

FIGS. 10 and 11 illustrate an exemplary embodiment of an anchoring mechanism 180 that can be used as the anchoring mechanism for any of the chordae support devices described herein for maintaining a device in its intended location relative to tissue or other heart structures. In particular, anchoring mechanism 180 is positioned at one end of a wire portion 182. Anchoring mechanism 180 comprises first and second discs 184, 186, each of which can be formed from a wire scaffold and may include material extending over the scaffold. These discs 184, 186 can be made of a shape memory material, such as Nitinol, and can be compressed until they are in their desired location relative to the heart, at which point the compression force can be removed to allow the discs to expand back toward their original shape and size. The discs 184, 186 can be positioned on opposite sides of a mitral leaflet 190, for example, as is illustrated in FIG. 11. After the discs 184, 186 are positioned on opposite sides of a tissue and allowed to expand, they can then be moved closer together in order to capture the tissue and secure the wire portion 182 in its final position relative to the patient's anatomy.

Figure 12:
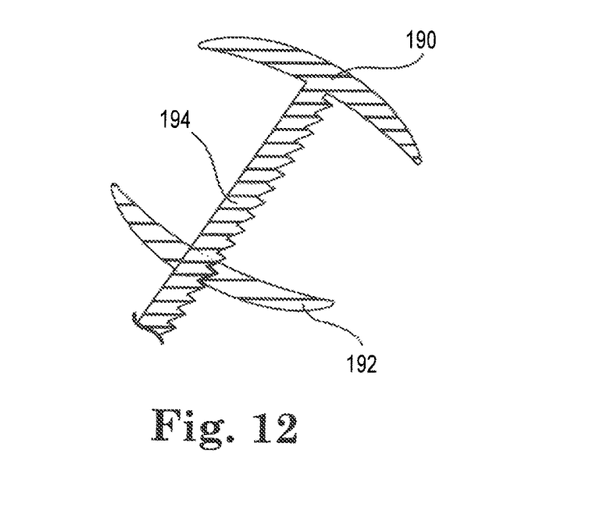
FIG. 12 is a cross-sectional front view of an embodiment of an anchoring device for securing a chordae support device to tissue.

FIG. 12 illustrates another exemplary manner of securing two discs 190, 192 relative to each other, wherein these discs can also be made of a self-expanding wire scaffold with a material covering, similar to the discs 184, 186 described above. In this embodiment, disc 190 is positioned at a distal end of a wire 194 and is fixed relative to it, while disc 192 is spaced from the distal end of wire 194 and disc 190, and is slideable along the wire 194 in a single direction. That is, wire 194 is structured in such a way that the movement of the disc 192 can only be in one direction (i.e., the movement of disc 192 is non-reversible), and is particularly illustrated here as having a series of angled teeth. An inner opening of disc 192 is structured to cooperate with this outer surface of wire 194 so that once the disc 192 is slid into its desired position relative to the disc 190, it cannot be slid in the opposite direction.

The devices of FIGS. 10-12 can be delivered to their desired location within the heart via a guide catheter having an outer sheath, for example. The device can be structured so that it pierces through the desired leaflet until the disc at the distal end of the wire is deployed or expanded. The outer sheath can then be pulled back further to expose the other disc, thereby allowing it to expand or deploy. Then, the wire can be pulled while the outer sheath is pushed, thereby pressing the two discs into closer proximity to each other.

Figure 13:
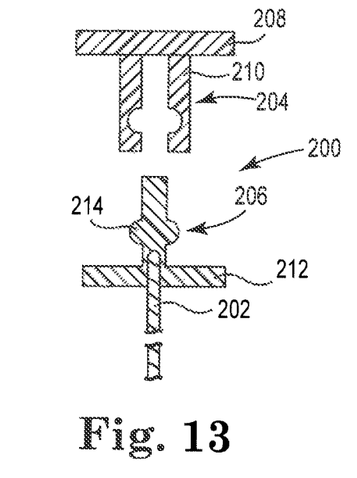
FIG. 13 is a cross-sectional front view of another embodiment of an anchoring device for securing a chordae support device to tissue.
Figure 14:
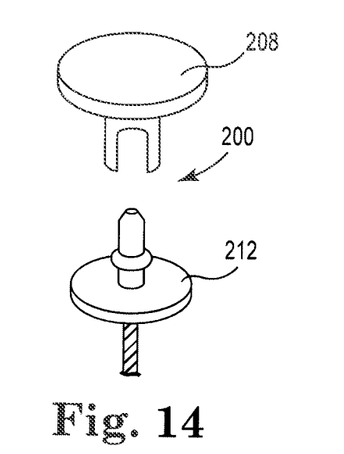
FIG. 14 is a perspective view of the anchoring device illustrated in FIG. 13.
Figure 15:
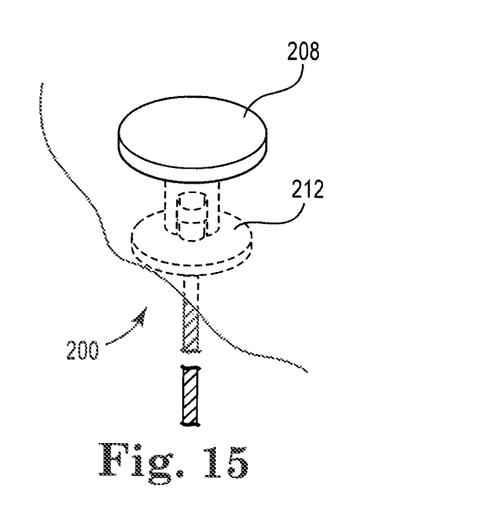
FIG. 15 is a schematic view of the anchoring device of FIGS. 13 and 14 positioned relative to a piece of tissue.

FIGS. 13-15 illustrate an exemplary embodiment of an anchoring mechanism 200 that can be used as the anchoring mechanism for any of the devices described herein for maintaining a device in its intended location relative to leaflets, tissue, or other heart structures. In particular, anchoring mechanism 200 is shown as being positioned at one end of a wire portion 202. Anchoring mechanism 200 includes first and second interlocking members 204, 206, which can be positioned on opposite sides of tissue, such as a mitral leaflet, in order to lock the anchoring mechanism 200 in place relative to the tissue. In particular, member 204 includes a plate 208 from which a deformable clamp 210 extends, while member 206 includes a plate 212 from which a post 214 extends. As shown, the inner area of clamp 210 includes contours that generally correspond with the outer surface contours of post 214 so that when these two components are pressed together, the inner area of clamp 210 interferes with the outer surface of post 214, which causes it to expand at least slightly outwardly. As the components are pressed together further, the clamp 210 will be able to move back toward its original shape, thereby securing it onto the post 214.

In order to provide a secure attachment to the tissue, the height of the clamp 210 and post 214 can be approximately the same as the thickness of the tissue to which they will be secured, for example. In this way, one or both of the plates 208, 212 will be in contact with the tissue, thereby helping to distribute the contact forces over a larger surface area of the tissue and helping to prevent the tissue from tearing and/or prevent the mechanism 200 from being unintentionally pulled through the tissue. Thus, in its final position, as is illustrated in FIG. 15, for example, the plates 208, 212 will be on opposite sides of the tissue, while the clamp 210 and attached post 214 will extend through a hole in the tissue. The members 204, 206 can be introduced into the heart by a tool via apical access, for example, although other access techniques are contemplated, in accordance with the invention.

Figure 16:
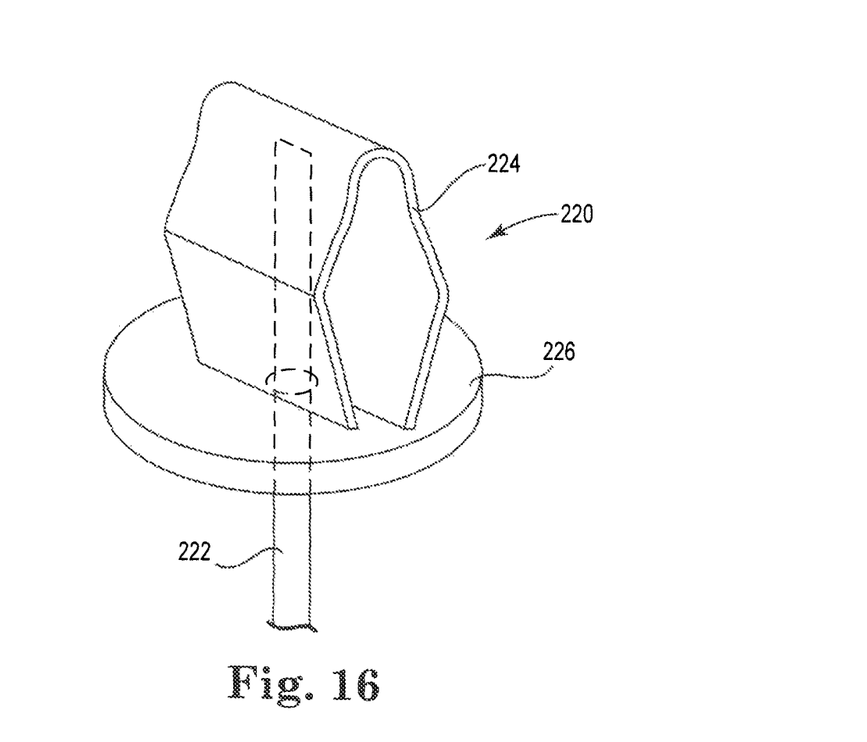
FIG. 16 is a schematic perspective view of another embodiment of an anchoring device for securing a chordae support device to tissue, with the anchoring device in its delivery configuration.
Figure 17:
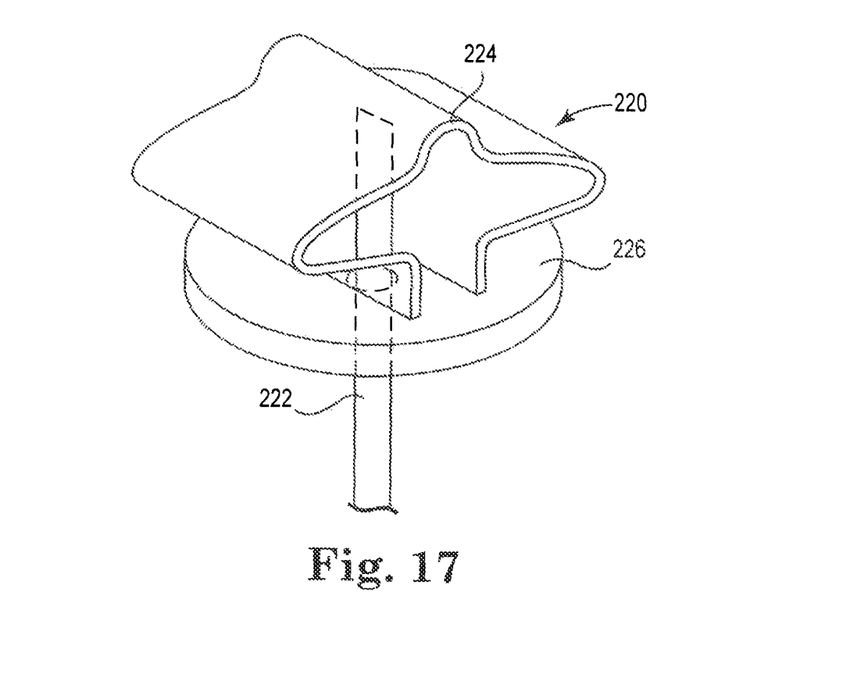
FIG. 17 is a schematic perspective view of the anchoring device of FIG. 16, illustrating the anchoring device in its deployed configuration.

FIGS. 16 and 17 illustrate an exemplary embodiment of an anchoring mechanism 220 that can be used as the anchoring mechanism for any of the devices described herein for maintaining a device in its intended location relative to tissue or other heart structures. In particular, anchoring mechanism 220 is shown as being positioned at one end of a pull cord or wire 222. Anchoring mechanism 220 includes a collapsible member 224 at a distal end of the pull cord 222 and a plate 226 adjacent to the collapsible member 224. Anchoring mechanism 220 can be introduced to the tissue to which it will be attached, such as a mitral valve leaflet, using an apical approach, for example. In any case, FIG. 16 illustrates the member 224 as it is configured prior to its deployment for securing it to tissue. The member 224 can be pushed through the tissue, either by piercing the tissue with a tip of the member 224, or by being pushed through an opening that was otherwise created in the tissue. After the member 224 is at least partially positioned on the opposite side of the tissue from the plate 226, the cord 222 can be pulled in a proximal direction to deform the member 224 in such a way that it creates a relatively large surface area to press against the tissue, as is illustrated in FIG. 17, for example. The pull cord 222 can then be attached to the heart in such a way that it helps to provide tension to the structure to which it is attached, such as a mitral valve leaflet.

Figure 18:
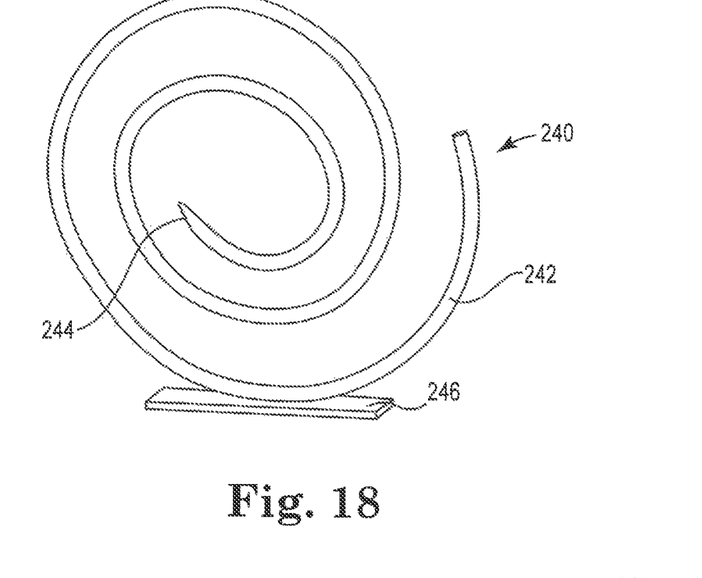
FIG. 18 is a perspective view of another embodiment of an anchoring device in its coiled configuration.
Figure 19:
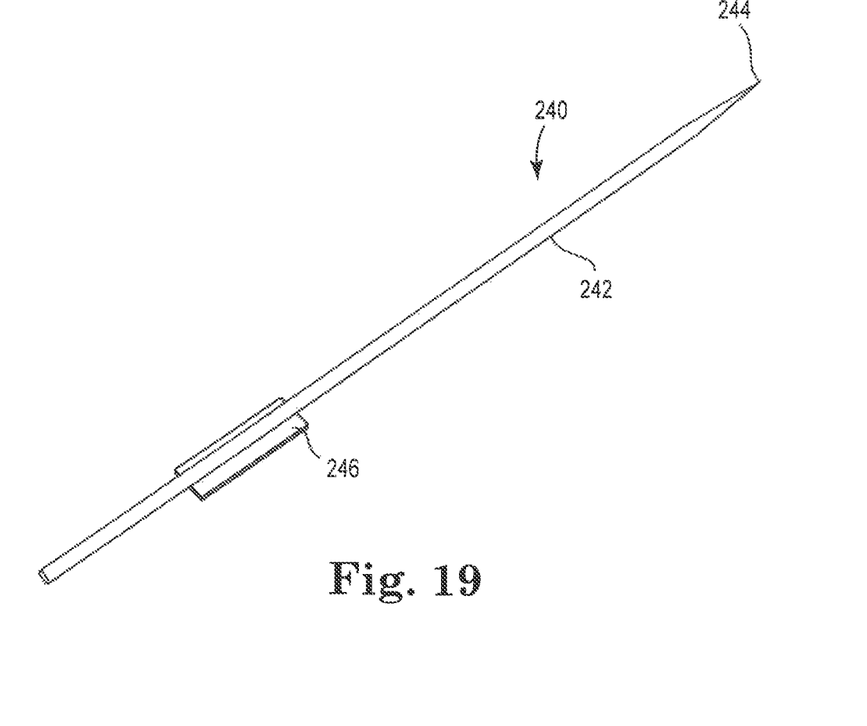
FIG. 19 is a perspective view of the anchoring device of FIG. 18 in its straightened configuration.

FIGS. 18 and 19 illustrate another exemplary embodiment of an anchoring mechanism 240 that can be used as the anchoring mechanism for attachment of any chordae support device to tissue. Anchoring mechanism 240 includes a wire 242 having a sharp end 244 for penetrating tissue, such as a valve wall and/or leaflet. Mechanism 240 further includes a plate 246 attached at a selected point along the length of the wire 242. The anchoring mechanism 240 is configured to be a "stapler" type of device that is made of a material having shape memory characteristics. Mechanism 240 is pre-shaped from a shape memory material, such as Nitinol, so that it takes on a coil or loop shape when in a relaxed position (see FIG. 18), but can be straightened by applying an appropriate external force (see FIG. 19).

In order to utilize this structure, the wire 242 is held in this straightened condition until it reaches a desired location within the patient and penetrates the desired tissue (e.g., a mitral valve leaflet). At this point, the external straightening force can be removed, thereby allowing the mechanism 240 to return to its coiled or looped shape in order to anchor it to the tissue of the valve wall. In one embodiment of a deployed state of the mechanism 240, the plate 246 will be positioned on one side of the tissue while the wire 242 will be positioned within and/or on the opposite side of that same tissue. In this way, the plate 246 will provide a load distribution over the surface of the leaflet to prevent it from pulling back through the tissue. It is understood that the mechanism 240 may be attached to a wire or cord that can attach to the papillary muscle of the heart, for example, in order to adjust the distance between the leaflet and the papillary muscle.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A chordae support device for repairing the native chordae of a heart valve, the device comprising:
    an elongated member having first and second ends;
    a first anchor extending from the first end of the elongated member, the first anchor comprising a first member fixed at the first end of the elongated member and a second member spaced from the first member, wherein the first and second members are configured to contact tissue when the first anchor is engaged, and wherein the second member in a deployed configuration is slideably moveable in one direction toward the first member along the elongated member; and
    a second anchor spaced from the first anchor and slideably moveable along the elongated member in only one direction toward the first anchor,
    wherein the first anchor is configured to engage the heart valve, wherein the second anchor is configured to engage a papillary muscle or an apex of a heart, and wherein a length of the elongated member between the first anchor and the second anchor following tissue engagement is adjustable in only one direction.

2. The chordae support device of claim 1, wherein the first anchor comprises a sharp tip for penetrating tissue.

3. The chordae support device of claim 1, wherein the first member is disc shaped, and wherein the second member is disc shaped.

4. The chordae support device of claim 1, wherein at least one of the first and second members comprises a shape memory material.

5. The chordae support device of claim 4, wherein the first and second members both comprise a shape memory material, and wherein the first and second members are compressible and expandable in response to the application or removal of external forces.

6. The chordae support device of claim 1, wherein the elongated member comprises a series of teeth that cooperate with an internal surface of the second member to allow movement of the second member in a first direction toward the first member and to prevent movement of the second member in a second direction away from the first member.

7. The chordae support device of claim 1, wherein the second anchor comprises a shape memory material.

8. The chordae support device of claim 1, wherein the second anchor comprises a ratcheting mechanism.

9. The chordae support device of claim 1, wherein the elongated member comprises a wire.

10. The chordae support device of claim 1, wherein the first and second members are configured to engage opposite sides of a heart valve leaflet.

* * * * *